(12) United States Patent
Wagner

(10) Patent No.: US 7,114,953 B1
(45) Date of Patent: *Oct. 3, 2006

(54) TOOTH WHITENING APPLIANCE HAVING MEMBRANE COVERED APPLICATOR

(76) Inventor: Eugene C. Wagner, 1626 Chastain Pkwy. East, Pacific Palisades, CA (US) 90272

( * ) Notice: Subject to any disclaimer, the term of this patent is extended or adjusted under 35 U.S.C. 154(b) by 0 days.

This patent is subject to a terminal disclaimer.

(21) Appl. No.: 10/998,705

(22) Filed: Nov. 29, 2004

Related U.S. Application Data

(63) Continuation-in-part of application No. 10/423,664, filed on Apr. 25, 2003, now Pat. No. 6,840,771.

(51) Int. Cl.
*A61C 15/00* (2006.01)

(52) U.S. Cl. ...................... 433/214; 433/216

(58) Field of Classification Search ............. 433/6, 433/80, 71, 215, 214, 216; 604/77
See application file for complete search history.

(56) References Cited

U.S. PATENT DOCUMENTS

| 516,529 | A | * | 3/1894 | Hansen | 433/71 |
|---|---|---|---|---|---|
| 2,171,695 | A | * | 9/1939 | Harper | 433/42 |
| 2,933,811 | A | * | 4/1960 | Lifton | 433/37 |
| 3,527,219 | A | | 9/1970 | Greenberg | |
| 3,567,823 | A | | 3/1971 | Yamaga | |
| 3,577,640 | A | * | 5/1971 | Lee | 433/60 |
| 3,624,909 | A | | 12/1971 | Greenberg | |
| 4,173,219 | A | | 11/1979 | Lentine | |
| 4,776,792 | A | | 10/1988 | Wagner | |
| 4,867,680 | A | * | 9/1989 | Hare et al. | 433/37 |
| 5,165,424 | A | | 11/1992 | Silverman | |
| 5,302,374 | A | | 4/1994 | Wagner | |
| 5,562,449 | A | | 10/1996 | Jacobs | |
| 5,566,684 | A | | 10/1996 | Wagner | |
| 5,575,654 | A | | 11/1996 | Fontenot | |
| 5,611,687 | A | | 3/1997 | Wagner | |
| 5,863,202 | A | | 1/1999 | Fontenot | |
| 5,891,453 | A | | 4/1999 | Sagel | |
| 5,989,569 | A | * | 11/1999 | Dirksing et al. | 424/401 |
| 6,096,328 | A | | 8/2000 | Sagel | |
| 6,126,443 | A | * | 10/2000 | Burgio | 433/215 |
| 6,274,122 | B1 | * | 8/2001 | McLaughlin | 424/53 |
| 6,364,665 | B1 | | 4/2002 | Trettenero | |
| 6,379,147 | B1 | | 4/2002 | Georgakis | |
| 6,422,868 | B1 | * | 7/2002 | Lindquist | 433/215 |
| 6,506,053 | B1 | | 1/2003 | Wiesel | |
| 6,514,484 | B1 | | 2/2003 | Rajaiah | |
| 6,517,350 | B1 | | 2/2003 | Diasti | |
| 6,896,518 | B1 | * | 5/2005 | Jacobs et al. | 433/215 |
| 6,948,936 | B1 | * | 9/2005 | Miller et al. | 433/214 |
| 2001/0044096 | A1 | | 11/2001 | Lindquist | |
| 2002/0081555 | A1 | * | 6/2002 | Wiesel | 433/215 |
| 2002/0146666 | A1 | * | 10/2002 | Sagel et al. | 433/215 |

(Continued)

*Primary Examiner*—Todd E. Manahan
(74) *Attorney, Agent, or Firm*—Seth Natter; Natter & Natter

(57) ABSTRACT

A tooth whitening appliance includes an applicator having a soft moldable core covered by a plastic film membrane. The contours of buccal surfaces of target teeth to be whitened are impressed into the applicator by applying lateral pressure. A layer of tooth whitening preparation is deposited on the impressions formed in the applicator and the applicator is repositioned against the buccal tooth surfaces for the administration of the tooth whitening preparation. The applicator core is soft and moldable preferably at or below body temperature. The membranes support the applicator in reduced thickness impression areas. The applicator core may be optionally preloaded with tooth whitening preparation.

19 Claims, 2 Drawing Sheets

U.S. PATENT DOCUMENTS

2003/0003421 A1*   1/2003  Bestenheider et al. ...... 433/215
2004/0110111 A1*   6/2004  Wasylucha .................. 433/29
2004/0131561 A1*   7/2004  McLaughlin ................. 424/53

* cited by examiner

TOOTH WHITENING APPLIANCE HAVING MEMBRANE COVERED APPLICATOR

RELATED APPLICATIONS

This application is a continuation-in-part of application Ser. No. 10/423,664 filed Apr. 25, 2003, now U.S. Pat. No. 6,840,771 issued Jan. 11, 2005.

BACKGROUND OF THE INVENTION

1. Field of the Invention

This invention relates generally to cosmetic tooth whitening and more particularly to an appliance having a membrane covered soft impressible applicator for even and efficacious delivery of a tooth whitening preparation to buccal surfaces of target teeth.

2. Antecedents of the Invention

Significant advances in the art of tooth whitening have evolved in recent years. Tooth whitening is no longer relegated to the costly and time consuming procedures rendered by the dental practitioner. Various approaches have evolved for practicing tooth whitening procedures without participation of the dental practitioner.

Among the early tooth whitening systems for do-it-yourself usage was a paste or gel containing a hydrogen peroxide or carbamide peroxide constituent. The gel or paste was applied to tooth surfaces by, for example, a toothbrush, a cotton swab, etc.

Unfortunately, such systems failed to provide readily noticeable results, due to a combination of factors including the limited time duration of application as well as the dilution of effective whitening or bleaching constituent within the oral cavity by saliva. Further, gingival surfaces were engaged by the whitening or bleaching constituent, leading to possible gingival initiation or other undesired effects.

Improved tooth whitening procedures included the admixture of conventional toothpaste together with a tooth whitening preparation, as described in U.S. Pat. No. 5,302,374 issued Apr. 12, 1994 and U.S. Pat. No. 5,597,554 issued Jan. 28, 1997 to applicant herein. The employment of such technique resulted in decreased tooth surface wear as well as an increase in the rate of efficacious release of the whitening or bleaching constituent of the tooth whitening preparation.

A further approach at providing an effective delivery system for a tooth whitening preparation on buccal enamel surfaces of target teeth included the system disclosed in U.S. Pat. No. 5,611,687 which issued Mar. 18, 1997 to applicant herein. Such system comprised and applicator for carrying and applying a liquid preparation solely upon buccal surfaces of target teeth, i.e. teeth which are visible when talking, smiling, etc. The liquid preparation was drawn to an applicator tip by capillary action. To administer a coating of the tooth whitening preparation on selected tooth enamel surfaces, the tip was wiped over the surfaces to be treated.

Other attempts for improving the self administration of tooth whitening preparations included utilizing a fitted dental trough which surrounded buccal, occlusal and lingual tooth surfaces, as disclosed in U.S. Pat. No. 5,165,424 issued Nov. 24, 1992. The system disclosed therein did not attain widespread commercial success, perhaps due to the fact that the device was ungainly and impeded speech. It could not, therefore, be worn in any environment wherein social encounters might be anticipated. Further, the device did not assure the administration of tooth whitening preparation on only selected tooth surfaces and only to selected target teeth.

A further approach comprised the utilization of flexible strips preloaded with a tooth whitening preparation, as disclosed in U.S. Pat. No. 5,891,453 issued Apr. 6, 1999. The flexible strips disclosed therein were unable to attain a true impression of the user's buccal dentition; it could not intimately enter interdental crevices, for example. Further, the user was not able to control the concentration of tooth whitening preparation or limit the application to selected target teeth or tooth surfaces. A further disadvantage was that the tooth whitening preparation was often in contact with gingival surfaces, which often led to gingival irritation.

SUMMARY OF THE INVENTION

A tooth whitening appliance comprises an applicator having a soft moldable core of formative material capable of receiving a dental impression. A plastic film stratum membrane covers the core.

The applicator is custom fitted by impressing the contours of buccal surfaces of target teeth into the applicator through the application of lateral pressure against an outer, i.e. buccal, face of the applicator. Impression taking may be facilitated by placement of the applicator in a carrier or jig having a plan configuration of a partial dentition arch. A lateral occlusal ledge may extend from the carrier.

Impressions of buccal surfaces of target teeth to be whitened are thus formed in an inner i.e. lingual, face of the applicator, with a buccal and a lingual membrane serving to maintain dimensional integrity and stability of the applicator in reduced thickness areas of the core.

The impressions thereafter receive a tooth whitening preparation which is deposited on the contoured surface of the lingual membrane. Alternatively or conjunctively, a tooth whitening preparation is applied to the buccal surfaces of the target teeth. Thereafter, the applicator is repositioned against the buccal surfaces of the target teeth to provide intimate undiluted engagement between the tooth whitening preparation and the buccal surfaces to be whitened.

Optionally, the core may be preloaded with tooth whitening preparation carried on a lingual face of the core or in wells, pockets or microcapsules and the lingual membrane may include perforations through which tooth whitening preparation is dispensed, or the preparation may be impregnated in lingual membrane perforations.

Separate applicators are fitted for the maxillary dentition and the mandibular dentition for simultaneous tooth whitening treatment of target teeth in both or the maxillary and mandibular dentitions may be treated individually.

From the foregoing compendium, it will be appreciated that it is an aspect of the present invention to provide a tooth whitening appliance having a membrane covered applicator of the general character described which is not subject to the disadvantages of the antecedents of the invention aforementioned.

It is a feature of the present invention to provide a tooth whitening appliance having a membrane covered applicator of the general character described having a simplified procedure for custom fitting.

A consideration of the present invention is to provide a tooth whitening appliance having a membrane covered applicator of the general character described which precludes undesirable gingival exposure to tooth whitening preparations.

A further aspect of the present invention is to provide a tooth whitening appliance having a membrane covered applicator of the general character described which assures against dilution of a tooth whitening preparation.

To provide a tooth whitening appliance having a membrane covered applicator of the general character described which does not impede speech is a further consideration of the present invention.

Another feature of the present invention is to provide a tooth whitening appliance having a membrane covered applicator of the general character described which is low in cost and suitable for manufacture by economical mass production fabrication.

To provide a tooth whitening appliance having a membrane covered applicator of the general character described which permits the user to vary the quantity of tooth whitening preparation applied to selected tooth surfaces is a further aspect of the present invention.

Another feature of the present invention is to provide a tooth whitening appliance having a membrane covered applicator of the general character described which is compatible with the administration of any of a number of available tooth whitening preparations.

A still further aspect of the present invention is to provide a tooth whitening appliance having a membrane covered applicator of the general character described which is both safe and efficacious.

Yet another feature of the present invention is to provide a tooth whitening appliance having a membrane covered applicator of the general character described which does not socially inhibit a user's movement from place to place during tooth whitening treatment.

Other aspects, features and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description and drawings and the scope of which will be more particularly pointed out and indicated in the appended claims.

BRIEF DESCRIPTION OF THE DRAWINGS

In the accompanying drawings, in which are shown some of the various exemplary embodiments of the invention.

DESCRIPTION OF THE PREFERRED EMBODIMENTS

Figure 1:
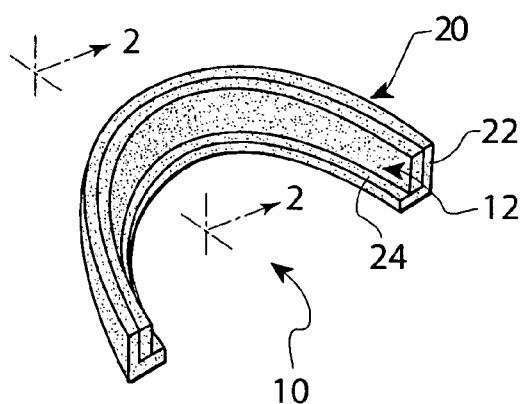
FIG. 1 is a perspective illustration of a tooth whitening appliance constructed in accordance with and embodying the invention prior to custom fitting and showing an applicator comprising a soft core opposed faces of which are covered with a plastic film membrane, with the applicator positioned in a carrier to facilitate molding impressions of buccal tooth surfaces to be whitened.

Incorporated herein by reference is my prior copending allowed application Ser. No. 10/429,664 filed Apr. 25, 2003.

Referring now in detail to the drawings, the reference numeral 10 denotes generally a tooth whitening appliance constructed in accordance with and embodying the invention. The tooth whitening appliance 10 provides efficacious tooth whitening of only selected surfaces, i.e. the surfaces which are visible when smiling or speaking, for example. Accordingly, the tooth whitening appliance 10 is configured for the whitening of buccal enamel surfaces of only target teeth, as will be exemplified hereinafter.

Pursuant to the invention, the tooth whitening appliance 10 includes an applicator 12 having a soft formative moldable core 14 of material suitable for employment in taking dental impressions.

Preferably, the core 14 is preferably clear or white and is formed of a nonreactive, inert material which is soft and pliable at or below body temperature. Suitable materials having such desired characteristics include various waxes employed in the dental field or available blends of waxes. Among the suitable dental waxes are utility waxes available from Sullivan-Schein Dental of Melville, N.Y., including Henry Schein® utility wax strips and Heraeus Kulzer utility wax strips, as well as soft orthodontic wax available from Kerr Corporation of Orange, Calif.

It is also within the ambit of the invention to employ materials which might require immersion in warm or hot water for softening. Suitable thermoplastics having rheological characteristics for implementation as the core 14 include thermoplastics which are deformable at temperatures below those which would cause discomfort or burning within the oral cavity during a fitting procedure, including those disclosed in U.S. Pat. No. 5,566,684 issued to applicant herein and U.S. Pat. No. 5,503,552.

The core 14 may be dimensioned as a strip initially having uniform thickness in the range of approximately 1 mm to 3 mm throughout and a height of approximately 10 mm to 15 mm. Pursuant to the invention, an outer or buccal face of the core 14 is overlaid with a thin plastic film stratum membrane 16. Similarly, an inner or lingual face of the core 14 is covered or overlaid by a thin plastic film stratum membrane 18. It is possible to overlay only one of the faces with a membrane.

The membranes 16, 18 may be comprised of clear self-adherent plastic films such as those commonly employed as food grade plastic wrap, including, but not limited to plastic films formed of low density polyethylene, polyvinyl chloride and polyvinylidene chloride.

The contours of the buccal tooth surfaces of target teeth are impressed into the lingual face of the applicator 12 by registering the applicator 12 against the buccal surfaces of target teeth of the maxillary or mandibular dentition and applying lateral forces in a lingual direction. One may employ digital pressure for the application of such forces or may employ a carrier or jig 20.

Figure 2:
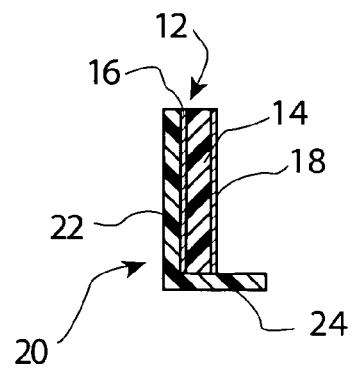
FIG. 2 is an enlarged scale sectional view through the appliance, the same taken substantially about the plane 2—2 of FIG. 1 and better illustrating the membrane covered core of the applicator and a transverse ledge which projects lingually from the carrier.

As illustrated in FIG. 2, the carrier 20 is generally "L" shaped in transverse cross section and includes an arcuate semi-cylindrical panel 22 and an integral perpendicular ledge 24. The ledge 24 may optionally extend upwardly toward the palate, such that the carrier 20 assumes the configuration of an impression tray.

The applicator 12 is placed against the inner face of the arcuate panel 22 with the buccal face membrane 16 abutting the arcuate panel 22. The carrier 20 preferably comprises a thermoplastic resin such as those disclosed in my copending application Ser. No. 10/429,664.

Figure 3:
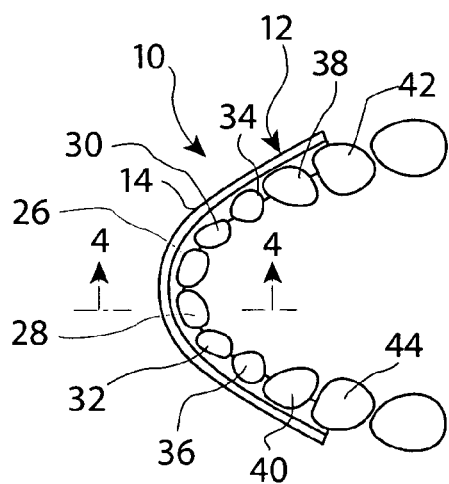
FIG. 3 is a bottom view of the appliance during fitting, with the carrier ledge omitted for clarity and showing the applicator in engagement with selected target teeth of a maxillary dentition for receiving impressions.

As heretofore mentioned, the tooth whitening appliance 10 is constructed to facilitate administration of a tooth whitening preparation only upon desired dentition surfaces which are normally exposed to view when one's mouth is opened or when one smiles. With reference to FIG. 3 comprising a bottom view of a maxillary dentition arch, it should be noted that the arch is generally symmetrically arrayed and includes at least a pair of central incisors 26, 28, a pair of lateral incisors 30, 32, a pair of cuspids 34, 36, a pair of first bicuspids 38, 40 and a pair of second bicuspids 42, 44.

Generally, the target teeth for tooth whitening comprise the central incisors 26, 28, the lateral incisors, 30, 32 the cuspids 34, 36 and the first bicuspids 38,40. For some people, tooth whitening may also be desirable on the buccal surfaces of the second bicuspids 42, 44.

The applicator 12 is provided in predetermined sizes; it may be furnished in varying lengths such as to accommodate the second bicuspids or may be provided of an extended length, with the user trimming both ends, such that the trimmed applicator will accommodate the target teeth. Additionally, the lingual face of the applicator 12 may include preformed tooth surface indentations for guidance in placement during the fitting procedure.

If the core 14 is required to be softened by heating, the applicator 12 is immersed in hot or warm water for a prescribed duration sufficient to heat the core 14 to a softened state, wherein it is readily pliable and capable of taking an impression of tooth surfaces. The appliance is then removed from the hot water, allowed to cool slightly, such that it will not burn tissue or cause discomfort when placed in the mouth, and thereafter impressed against buccal surfaces of the target teeth through the application of lateral pressure in a lingual direction against the buccal face of the applicator 12 until it assumes a position illustrated in FIG. 3, wherein the core 14 has conformed to the buccal surfaces of the target teeth and entered interdental intertistices. It should be noted that if the carrier 20 is employed during the fitting procedure, the ledge 24 serves as a guide, engaging and sliding under maxillary or over mandibular occlusal surfaces.

If a soft wax or other soft core material which does not require elevated temperature to receive buccal tooth surface impressions is employed, the aforementioned heating and cooling steps are unnecessary. Further, employment of the carrier 20 is not mandatory and the applicator may be fitted utilizing only digital manipulation.

Figure 4:
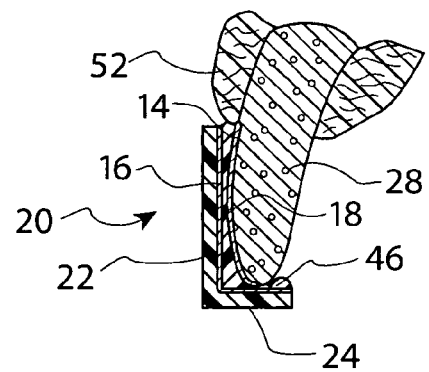
FIG. 4 is an enlarged scale sectional view, the same being taken substantially along the plane 4—4 of FIG. 3 and showing the inner face of the applicator contoured with the impression of the buccal surface of a user's central incisor.

With reference now to FIG. 4, it will be seen that a portion or portions of the core 14 may extrude between the occlusal tooth surfaces and the ledge 24 and form a bead 46 on the lingual face of a tooth 28. The bead 46 serves to retain or lock the applicator 12 in its fitted position so as not to impede speech or other functions when being worn during administration of the tooth whitening preparation.

Figure 5:
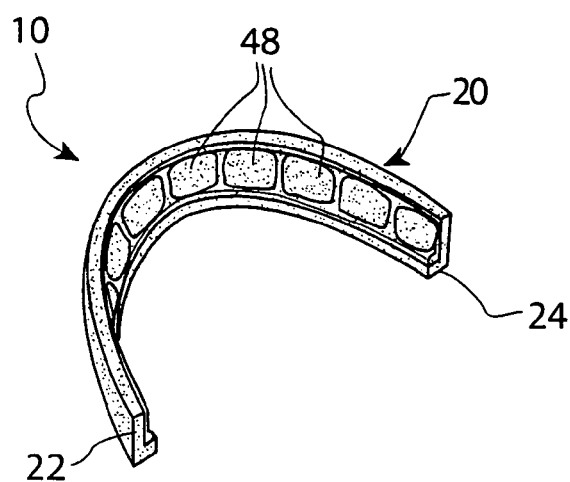
FIG. 5 is a perspective view of the tooth whitening appliance after fitting and illustrating impressed contours of buccal surfaces of the user's target teeth on a lingual membrane covered face of the applicator.
Figure 6:
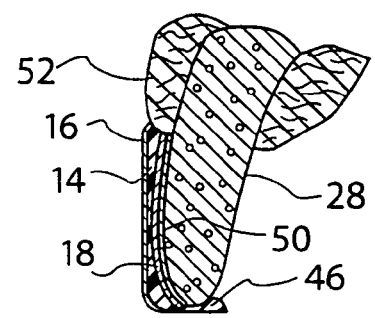
FIG. 6 is a sectional view, similar to FIG. 4, illustrating the applicator in use during the administration of a tooth whitening preparation.

After fitting, the applicator 12 is removed from the oral cavity, with the inner lingual face of the core 14 bearing impressions 48 of the buccal tooth surfaces, as illustrated in FIG. 5. If the carrier 20 was employed, the applicator 12 is stripped from the carrier.

Thereafter, a layer or coating 50 of any of a number of available tooth whitening preparations including pastes, liquids and gels or combinations thereof may be applied to the membrane 18 at some or all of the impressions 48 and the applicator 12 is placed against the buccal tooth surfaces of the target teeth to administer the tooth whitening preparation.

Alternatively or conjunctively, a layer or coating 50 of tooth whitening preparation may be applied to the buccal enamel surfaces of the target teeth before the applicator is positioned for administration of tooth whitening preparation.

The applicator is maintained in its administration position, assuring intimate contact between the layer 50 of the tooth whitening preparation and the buccal enamel surfaces of the target teeth for a prescribed treatment duration. The fitted applicator 12 may be reused indefinitely to administer tooth whitening preparation in successive treatments.

Notably, the applicator 12 assures that the tooth whitening preparation will not inadvertently contact and possibly irritate gingival surfaces 52 and also assures that the tooth whitening preparation itself will not be subject to dilution or diminution in effectiveness resulting from contact with saliva.

The membranes 16, 18 constitute a smooth liquid impervious inert contact surface on both the buccal and lingual faces of the applicator 12 and significantly serve to provide dimensional integrity and stability to the applicator in impression areas 48, wherein the core 14 has been thinned during the fitting procedure. In some areas, the membranes may provide the sole supporting medium for carrying the coating 50 of tooth whitening preparation 10.

It should be recognized that the membrane 18 may be precoated with a tooth whitening preparation, such as a gel, prior to fitting. In such instances, the applicator 12 is not removed after fitting and remains in place for one step fitting and administration of the tooth whitening preparation.

Figure 7:
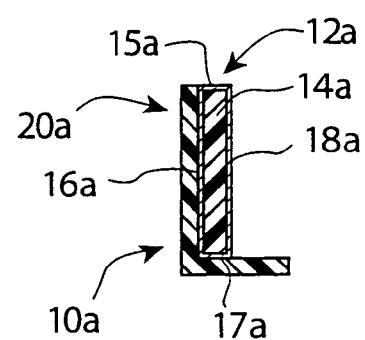
FIG. 7 is an enlarged scale sectional view, similar to FIG. 2, of a modified applicator seated in a carrier prior to receiving impressions and wherein all surfaces of the applicator core are covered with a plastic film membrane.

In FIG. 7 there is illustrated the alternate embodiment of the invention wherein like numerals have been employed to designate like components of the previous embodiment, however, bearing the suffix "a". A tooth whitening appliance 10a includes applicator 12a having a core 14a. The core 14a is completely enveloped by a membrane which includes a lingual face portion 16a, a buccal face portion 18a as well as top and bottom edge portions 15a, 17a respectively. A carrier 20a identical to the carrier 20 is also illustrated.

Figure 8:
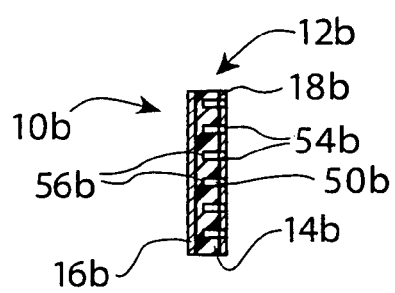
FIG. 8 is an enlarged scale sectional view, similar to the views of FIGS. 2 and 7, through a further embodiment of the invention, wherein an applicator is preloaded with tooth whitening preparation and a lingual membrane includes perforations.

In FIG. 8 there is illustrated a further embodiment of the invention wherein like numerals have been employed to designate like components of the prior embodiments, however, bearing the suffix "b".

An applicator 12b is preloaded, i.e. impregnated, with tooth whitening preparation in either liquid, paste, gel or dry format, such that it remains in place after fitting for one step fitting and tooth whitening.

The applicator 12b includes a soft moldable core 14b having a plastic film membrane 16b covering a buccal face of the applicator and a plastic film membrane 18b covering a lingual face of the applicator.

The lingual membrane 18b includes a plurality of perforations 54b and the core 14b includes a plurality of wells or pockets 56b which are open to the membrane 18b. Each well or pocket 56b carries a quantity 50b of tooth whitening preparation which is extruded through the perforations.

Alternately, the wells or pockets 56b may carry microcapsules of tooth whitening preparation or the microcapsules may be embedded throughout the core 14b. The microcapsules rupture, releasing the tooth whitening preparation through the perforations when lateral fitting force is applied and the applicator 12b is deformed to receive tooth impressions. A further or alternate construction utilizes the perforations 54b to carry the tooth whitening preparation and/or the tooth whitening preparation is coated on the core or the core side of the membrane 18b and passes through the perforation 54b.

Thus it will be seen that there is provided a tooth whitening appliance having a membrane covered applicator which achieves the various aspects, features and considerations of the present invention and which is well adapted to meet the conditions of practical usage.

Since various possible embodiments might be made of the present invention and since various changes might be made in the exemplary embodiments set forth herein without departing from the spirit of the invention, is to be understood that all matter herein described or shown in the accompanying drawings is to be interpreted as illustrative and not in a limiting sense.

Having thus described the invention, there is claimed as new and desired to be secured by Letters Patent:

1. A tooth whitening appliance comprising an applicator and a carrier, the applicator being positioned on the carrier, the applicator having a core, the core comprising a formative wax capable of receiving a dental impression, the wax being soft and moldable at or below body temperature, the applicator having a buccal face and a lingual face, at least one of the faces being overlaid with a plastic film membrane, the carrier comprising a panel and a transverse ledge extending from the panel, the ledge having a free distal edge, the panel and the ledge defining a substantially "L" shaped transverse cross section throughout the carrier.

2. A tooth whitening appliance for the administration of a tooth whitening preparation as constructed in accordance with claim 1 wherein the lingual face and the buccal face of the applicator are overlaid with a plastic film membrane.

3. A tooth whitening appliance in accordance with claim 1 wherein the panel is semi-cylindrical.

4. A tooth whitening appliance as constructed in accordance with claim 1 wherein the applicator core abuts the carrier panel.

5. A tooth whitening appliance for the administration of a tooth whitening preparation as constructed in accordance with claim 1 wherein the plastic film membrane comprises a thermoplastic selected from the group consisting of low density polyethylene, polyvinyl chloride and polyvinylidene chloride.

6. A tooth whitening appliance for the administration of a tooth whitening preparation as constructed in accordance with claim 1 wherein the lingual face of the applicator includes impressions of buccal surfaces of the target teeth, the appliance being positioned in an oral cavity with the impressions being registered with the corresponding buccal surfaces, a layer of tooth whitening preparation being positioned between the buccal surfaces and the corresponding surfaces of the impressions.

7. A tooth whitening appliance for the administration of a tooth whitening preparation as constructed in accordance with claim 6 wherein the layer of tooth whitening preparation is positioned between the buccal surfaces and the plastic film membrane.

8. A tooth whitening appliance for the administration of a tooth whitening preparation as constructed in accordance with claim 1 wherein the plastic film membrane overlies the lingual face of the applicator, the plastic film membrane including perforations, the perforations carrying a tooth whitening preparation.

9. A tooth whitening appliance for the administration of a tooth whitening preparation as constructed in accordance with claim 1 wherein the core carries a tooth whitening preparation, the tooth whitening preparation being released from the core when the applicator receives impressions of the buccal surfaces of the target teeth.

10. A tooth whitening appliance for the administration of a tooth whitening preparation as constructed in accordance with claim 9 wherein the tooth whitening preparation is carried in a plurality of pockets formed in the core.

11. A tooth whitening appliance for the administration of a tooth whitening preparation as constructed in accordance with claim 10 wherein the plastic film membrane overlies the lingual face of the applicator, the plastic film membrane including perforations.

12. A tooth whitening appliance for the administration of a tooth whitening preparation as constructed in accordance with claim 9 wherein the core carries a plurality of microcapsules, the tooth whitening preparation being released from the microcapsules when the applicator receives impressions of the buccal surfaces of the target teeth.

13. A tooth whitening appliance for the administration of a tooth whitening preparation as constructed in accordance with claim 12 wherein the plastic film membrane overlies the lingual face of the applicator, the plastic film membrane including perforations.

14. A method of whitening teeth utilizing a tooth whitening preparation, the method comprising the steps of:
   a) providing an appliance having a carrier with a substantially "L" shaped transverse cross section and an applicator having a core with rheological characteristics suitable for implementation as a dental impression material,
   b) adhering a plastic film membrane over at least one face of the applicator,
   c) obtaining in the one face of the applicator impressions of buccal surfaces of selected target teeth by inserting the carrier and the applicator in an oral cavity and applying lateral pressure against the carrier to force the applicator against the buccal surfaces of the selected target teeth,
   d) removing the carrier and applicator from the oral cavity after the impressions have been taken,
   e) separating the carrier from the applicator, and
   f) administering the preparation to the buccal surfaces by covering the buccal surfaces with the applicator and with a layer of preparation positioned between the buccal surfaces and the impressions formed in the one face of applicator.

15. A method in accordance with claim 14 wherein the step of administering the preparation includes applying a layer of preparation to the impressions of buccal surfaces formed in the applicator and thereafter covering the buccal surfaces of the selected target teeth with the applicator.

16. A method in accordance with claim 14 wherein the layer of preparation is positioned between the buccal surfaces and the plastic film membrane.

17. A method in accordance with claim 14 wherein the applicator includes two faces and the step of overlying a plastic film membrane comprises overlying a plastic film membrane over each face of the applicator.

18. A method of whitening teeth utilizing a tooth whitening preparation, the method comprising the steps of:
 a) providing an appliance having a carrier with a substantially "L" shaped transverse cross section throughout and an applicator having a core with theological characteristics suitable for implementation as a dental impression material,
 b) adhering a plastic film membrane over at least one face of the applicator,
 c) obtaining in the applicator impressions of buccal surfaces of selected target teeth by inserting the applicator in an oral cavity and applying lateral pressure against the carrier to force the applicator against the buccal surfaces of the selected target teeth,
 d) positioning a layer of preparation between the buccal surfaces and the impressions formed in the applicator.

19. A method of whitening teeth utilizing a tooth whitening preparation in accordance with claim 18 wherein the preparation is carried in the applicator and the membrane is perforated, the step of positioning including:
 i) extruding the tooth whitening preparation through the perforations.

* * * * *